(12) United States Patent
Kuribayashi et al.

(10) Patent No.: US 8,404,822 B2
(45) Date of Patent: Mar. 26, 2013

(54) PROBE, PROBE SET, PROBE-IMMOBILIZED CARRIER, AND GENETIC TESTING METHOD

(75) Inventors: Hideto Kuribayashi, Saga (JP); Toshifumi Fukui, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 482 days.

(21) Appl. No.: 12/294,915

(22) PCT Filed: Mar. 30, 2007

(86) PCT No.: PCT/JP2007/057705
§ 371 (c)(1),
(2), (4) Date: Sep. 15, 2010

(87) PCT Pub. No.: WO2007/114508
PCT Pub. Date: Oct. 11, 2007

(65) Prior Publication Data
US 2011/0003283 A1    Jan. 6, 2011

(30) Foreign Application Priority Data

Mar. 31, 2006  (JP) .................................. 2006-098675

(51) Int. Cl.
*C12Q 1/68* (2006.01)
*C12P 19/34* (2006.01)
*C07H 21/02* (2006.01)
*C07H 21/04* (2006.01)

(52) U.S. Cl. .... 536/23.1; 435/6.1; 435/91.2; 536/24.33; 536/24.32

(58) Field of Classification Search ........................ None
See application file for complete search history.

(56) References Cited

U.S. PATENT DOCUMENTS

| | | | | |
|---|---|---|---|---|
| 5,474,796 A * | 12/1995 | Brennan | ........... | 427/2.13 |
| 5,512,446 A | 4/1996 | Miyazaki et al. | | |
| 5,700,647 A | 12/1997 | Miyazaki et al. | | |
| 5,846,730 A | 12/1998 | Miyazaki et al. | | |
| 6,582,908 B2 * | 6/2003 | Fodor et al. | ........... | 506/9 |
| 6,773,882 B2 * | 8/2004 | Hogan et al. | ........... | 435/6.15 |
| 2004/0241643 A1 | 12/2004 | Yamamoto et al. | | |
| 2006/0046246 A1 * | 3/2006 | Zeng et al. | ........... | 435/5 |
| 2007/0134702 A1 | 6/2007 | Fukui et al. | | |
| 2008/0113363 A1 | 5/2008 | Fukui et al. | | |
| 2008/0113364 A1 | 5/2008 | Fukui et al. | | |
| 2008/0113365 A1 | 5/2008 | Kuribayashi et al. | | |
| 2008/0113366 A1 | 5/2008 | Kuribayashi et al. | | |
| 2008/0124733 A1 | 5/2008 | Fukui et al. | | |
| 2008/0161192 A1 | 7/2008 | Yoshii et al. | | |
| 2008/0286791 A1 | 11/2008 | Tomatsu et al. | | |
| 2008/0286792 A1 | 11/2008 | Tomatsu et al. | | |
| 2008/0287312 A1 | 11/2008 | Tomatsu et al. | | |
| 2008/0293061 A1 | 11/2008 | Tomatsu et al. | | |
| 2008/0293062 A1 | 11/2008 | Tomatsu et al. | | |
| 2008/0293063 A1 | 11/2008 | Tomatsu et al. | | |
| 2008/0293064 A1 | 11/2008 | Tomatsu et al. | | |
| 2008/0293065 A1 | 11/2008 | Tomatsu et al. | | |
| 2008/0293066 A1 | 11/2008 | Tomatsu et al. | | |
| 2008/0293067 A1 | 11/2008 | Tomatsu et al. | | |
| 2008/0299569 A1 | 12/2008 | Tomatsu et al. | | |
| 2008/0299570 A1 | 12/2008 | Tomatsu et al. | | |
| 2008/0299571 A1 | 12/2008 | Tomatsu et al. | | |
| 2008/0299572 A1 | 12/2008 | Tomatsu et al. | | |
| 2008/0299573 A1 | 12/2008 | Tomatsu et al. | | |
| 2008/0299574 A1 | 12/2008 | Tomatsu et al. | | |
| 2008/0299575 A1 | 12/2008 | Tomatsu et al. | | |
| 2008/0299576 A1 | 12/2008 | Tomatsu et al. | | |
| 2008/0299577 A1 | 12/2008 | Tomatsu et al. | | |
| 2008/0299578 A1 | 12/2008 | Tomatsu et al. | | |
| 2008/0305487 A1 | 12/2008 | Tomatsu et al. | | |
| 2008/0305488 A1 | 12/2008 | Tomatsu et al. | | |
| 2009/0004659 A1 | 1/2009 | Tomatsu et al. | | |
| 2009/0011419 A1 | 1/2009 | Tomatsu et al. | | |

FOREIGN PATENT DOCUMENTS

| | | |
|---|---|---|
| JP | 8-89254 | 4/1996 |
| JP | 2004-313181 | 11/2004 |
| JP | 2006-55028 | 3/2006 |

OTHER PUBLICATIONS

GenBank Accession No. DQ029045 Jul. 21, 2005 NCBI website.*
U.S. Appl. No. 12/295,276, filed Mar. 30, 2007, Applicants: Hideto Kuribayashi, et al.
U.S. Appl. No. 12/295,277, filed Mar. 30, 2007, Applicants: Toshifumi Fukui, et al.
U.S. Appl. No. 12/295,273, filed Mar. 30, 2007, Applicants: Hideto Kuribayashi, et al.
U.S. Appl. No. 12/294,910, filed Mar. 30, 2007, Applicants: Hideto Kuribayashi, et al.
U.S. Appl. No. 12/294,914, filed Mar. 30, 2007, Applicants: Toshifumi Fukui, et al.
U.S. Appl. No. 12/295,581, filed Mar. 30, 2007, Applicant(s): Hideto Kuribayashi, et al.
U.S. Appl. No. 12/295,584, filed Mar. 30, 2007, Applicant(s): Toshifumi Fukui, et al.
U.S. Appl. No. 12/295,583, filed Mar. 30, 2007, Applicant(s): Toshifumi Fukui, et al.
U.S. Appl. No. 12/295,579, filed Mar. 30, 2007, Applicant(s): Toshifumi Fukui, et al.
U.S. Appl. No. 11/935,930, filed Nov. 6, 2007, Applicant(s): Hiroto Yoshii, et al.
U.S. Appl. No. 11/935,807, filed Nov. 6, 2007, Applicant(s): Hideto Kuribayashi, et al.
U.S. Appl. No. 11/935,789, filed Nov. 6, 2007, Applicant(s): Toshifumi Fukui, et al.
U.S. Appl. No. 11/935,820, filed Nov. 6, 2007, Applicant(s): Hideto Kuribayashi, et al.
U.S. Appl. No. 11/935,849, filed Nov. 6, 2007, Applicant(s): Hiroto Yoshii, et al.

(Continued)

*Primary Examiner* — Katherine Salmon
(74) *Attorney, Agent, or Firm* — Fitzpatrick, Cella, Harper & Scinto

(57) ABSTRACT

A nucleic acid probe for classification of pathogenic bacterial species is capable of collectively detecting bacterial strains of the same species and differentially detecting them from other bacterial species. Any one of the base sequences of SEQ ID NO. 55 or a combination of at least two of them is used for detecting the gene of an infectious disease pathogenic bacterium.

7 Claims, 1 Drawing Sheet

OTHER PUBLICATIONS

U.S. Appl. No. 12/120,172, filed May 13, 2008, Applicant(s): Nobuhiro Tomatsu, et al.
U.S. Appl. No. 12/120,177, filed May 13, 2008, Applicant(s): Toshifumi Fukui, et al.
U.S. Appl. No. 12/120,104, filed May 13, 2008, Applicant(s): Nobuhiro Tomatsu, et al.
Song, et al., "16S Ribosomal DNA Sequence-Based Analysis of Clinically Significant Gram-Positive Anaerobiic Cocci", Journal of Clinical Microbiology, vol. 41, No. 4, Apr. 2003, p. 1363-1369 (2003).
Database DDBJ/EMBL/GenBank[on line], Accession No. AF542228, 2003.
PCT International Search Report and Written Opinion of the International Searching Authority in International Application No. PCT/JP2007/057705, Mailing Date Jul. 3, 2007.

* cited by examiner

FIG. 1

1st PCR PROTOCOL

| | | |
|---|---|---|
| 95°C | 600sec | |
| 92°C | 045sec | ⎫ |
| 72°C | 090sec | ⎬ 39CYCLE |
| 72°C | 600sec | |
| 04°C or r.t. | HOLD | |

FIG. 2

2nd PCR PROTOCOL

| | | |
|---|---|---|
| 95°C | 600sec | |
| 92°C | 045sec | ⎫ |
| 65°C | 045sec | ⎬ 24CYCLE |
| 72°C | 045sec | |
| 72°C | 600sec | |
| 04°C or r.t. | HOLD | |

PROBE, PROBE SET, PROBE-IMMOBILIZED CARRIER, AND GENETIC TESTING METHOD

TECHNICAL FIELD

The present invention relates to a probe and a probe set for detecting a gene of infectious disease pathogenic bacterium, *Peptoniphilus asaccharolyticus*, which are useful for detection and identification of the causative organism of an infectious disease, a probe-immobilized carrier on which the probe or the probe set is immobilized, a genetic testing method using the probe-immobilized carrier, and a genetic testing kit to be used for the method.

BACKGROUND ART

Heretofore, reagents for and methods of quickly and accurately detecting the causative organisms of infectious diseases in analytes have been proposed. For instance, Japanese Patent Application Laid-Open No. H08-89254 discloses oligonucleotides having specific base sequences, which can be respectively used as probes and primers for detecting pathogenic bacteria of candidiasis and aspergillosis, and a method of detecting target bacteria using such oligonucleotides. In addition, the same patent document also discloses a set of primers used for concurrently amplifying a plurality of target bacteria by PCR. In other words, those primers are used for the PCR amplification of nucleic acid fragments from fungi, which serve as a plurality of targets, in an analyte. The presence or absence of sequence portions, which are specific to the respective fungi, in the nucleic acid fragments amplified by the respective primers can be detected by a hybridization assay using probes specific to the respective fungi to identify fungal species in the analyte.

On the other hand, as a method capable of simultaneously detecting a plurality of oligonucleotides having different base sequences, there has been known a method using a probe array in which probes having sequences complementary to the respective base sequences are arranged at intervals on a solid support (Japanese Patent Application Laid-Open No. 2004-313181).

DISCLOSURE OF THE INVENTION

However, it is no easy task to establish a probe for specifically detecting a gene of an infectious disease pathogenic bacterium in a sample. That is, as well as the target gene, the sample may further contain genes of other infectious disease pathogenic bacteria. Thus, it is no easy task to establish the probe that specifically detects the gene of the infectious disease pathogenic bacterium while suppressing the influence of the presence of the genes of other infectious disease pathogenic bacteria (cross contamination). Under such circumstances, the inventors of the present invention have studied for obtaining a probe which allows accurate detection of a gene of an infectious disease pathogenic bacterium as mentioned hereinbelow while maintaining the cross contamination level low even when a sample in which genes of different bacteria are present is used. As a result, the inventors of the present invention have finally found a plurality of probes capable of precisely detecting the gene of the infectious disease pathogenic bacterium, *Peptoniphilus asaccharolyticus*.

A first object of the present invention is to provide a probe and a probe set, which can precisely identify a gene of a target bacterium. Another object of the present invention is to provide a probe-immobilized carrier which can be used for precisely identifying a target bacterium from an analyte in which various bacteria are concurrently present. Still another object of the present invention is to provide a genetic testing method for detecting a target bacterium, which can quickly and precisely detect various bacteria in an analyte when they are present therein, and a kit for such a method.

The probe for detecting a gene of infectious disease pathogenic bacterium, *Peptoniphilus asaccharolyticus*, of the present invention has the following base sequence (1) or (2):

(1) GAGTACGTGCGCAAGCATGAAACT (SEQ ID NO. 55) or a complementary sequence thereof; and (2) a modified sequence prepared such that any one of the sequences of SEQ ID NO. 55 and the complementary sequences thereof is subjected to base deletion, substitution, or addition as far as the modified sequence retains a function as the probe.

The characteristic feature of the probe-immobilized carrier of the present invention is that at least a probe having the above-mentioned base sequence (1) or (2) is immobilized on a solid-phase carrier, and when a plurality of probes including the above probe are employed, the respective probes are arranged at intervals.

The method of detecting a gene of an infectious disease pathogenic bacterium in an analyte by using a probe-immobilized carrier of the present invention includes the steps of:

(i) reacting the analyte with the probe-immobilized carrier having the above-mentioned constitution; and (ii) detecting the presence or absence of a reaction of the probe on the probe-immobilized carrier with a nucleic acid in the analyte, or detecting the strength of a reaction of the probe on the probe-immobilized carrier with a nucleic acid in the analyte.

The characteristic feature of the kit for detecting an infectious disease pathogenic bacterium of the present invention is to include a probe having the above-mentioned base sequence (1) or (2), and a reagent for detecting a reaction between the probe with a target nucleic acid.

According to the present invention, when an analyte is infected with the above-mentioned causative bacterium, the bacterium can be more quickly and precisely identified from the analyte even if the analyte is simultaneously and complexly infected with other bacteria in addition to the above-mentioned bacterium. In particular, *Peptoniphilus asaccharolyticus* can be detected while precisely distinguishing it from *Anaerococcus prevotii* which may otherwise cause cross contamination.

Further features of the present invention will become apparent from the following description of exemplary embodiments with reference to the attached drawings.

BRIEF DESCRIPTION OF THE DRAWINGS

FIG. 1 is a diagram illustrating a 1st PCR protocol.
FIG. 2 is a diagram illustrating a 2nd PCR protocol.

BEST MODE FOR CARRYING OUT THE INVENTION

The inventors of the present invention have obtained almost all of bacteria (represented by (1) to (62) below), which have been known as septicemia pathogenic bacteria so far, from the respective depository institutions and identified the 16S rRNA gene sequences of all the bacteria.

Subsequently, while making a comparison of all the identified sequences, probe sequences for *Peptoniphilus asaccharolyticus* were investigated in detail and the probes of the present invention, which can identify *Peptoniphilus asaccharolyticus*, have finally been found out.

| (1) *Staphylococcus aureus* | (ATCC12600) |
|---|---|
| (2) *Staphylococcus epidermidis* | (ATCC14990) |
| (3) *Escherichia coli* | (ATCC11775) |
| (4) *Klebsiella pneumoniae* | (ATCC13883) |
| (5) *Pseudomonas aeruginosa* | (ATCC10145) |
| (6) *Serratia marcescens* | (ATCC13380) |
| (7) *Streptococcus pneumoniae* | (ATCC33400) |
| (8) *Haemophilus influenzae* | (ATCC33391) |
| (9) *Enterobacter cloacae* | (ATCC13047) |
| (10) *Enterococcus faecalis* | (ATCC19433) |
| (11) *Staphylococcus haemolyticus* | (ATCC29970) |
| (12) *Staphylococcus hominis* | (ATCC27844) |
| (13) *Staphylococcus saprophyticus* | (ATCC15305) |
| (14) *Streptococcus agalactiae* | (ATCC13813) |
| (15) *Streptococcus mutans* | (ATCC25175) |
| (16) *Streptococcus pyogenes* | (ATCC12344) |
| (17) *Streptococcus sanguinis* | (ATCC10556) |
| (18) *Enterococcus avium* | (JCM8722) |
| (19) *Enterococcus faecium* | (ATCC19434) |
| (20) *Pseudomonas fluorescens* | (ATCC13525) |
| (21) *Pseudomonas putida* | (ATCC12633) |
| (22) *Burkholderia cepacia* | (JCM5964) |
| (23) *Stenotrophomonas maltophilia* | (ATCC13637) |
| (24) *Acinetobacter baumannii* | (ATCC19606) |
| (25) *Acinetobacter calcoaceticus* | (ATCC23055) |
| (26) *Achromobacter xylosoxidans* | (ATCC27061) |
| (27) *Vibrio vulnificus* | (ATCC27562) |
| (28) *Salmonella choleraesuis* | (JCM1651) |
| (29) *Citrobacter freundii* | (ATCC8090) |
| (30) *Klebsiella oxytoca* | (ATCC13182) |
| (31) *Enterobacter aerogenes* | (ATCC13048) |
| (32) *Hafnia alvei* | (ATCC13337) |
| (33) *Serratia liquefaciens* | (ATCC27592) |
| (34) *Proteus mirabilis* | (ATCC29906) |
| (35) *Proteus vulgaris* | (ATCC33420) |
| (36) *Morganella morganii* | (ATCC25830) |
| (37) *Providencia rettgeri* | (JCM1675) |
| (38) *Aeromonas hydrophila* | (JCM1027) |
| (39) *Aeromonas sobria* | (ATCC43979) |
| (40) *Gardnerella vaginalis* | (ATCC14018) |
| (41) *Corynebacterium diphtheriae* | (ATCC2701) |
| (42) *Legionella pneumophila* | (ATCC33152) |
| (43) *Bacillus cereus* | (ATCC14579) |
| (44) *Bacillus subtilis* | (ATCC6051) |
| (45) *Mycobacterium kansasii* | (ATCC12478) |
| (46) *Mycobacterium intracellulare* | (ATCC13950) |
| (47) *Mycobacterium chelonae* | (ATCC35752) |
| (48) *Nocardia asteroids* | (ATCC19247) |
| (49) *Bacteroides fragilis* | (JCM11019) |
| (50) *Bacteroides thetaiotaomicron* | (JCM5827) |
| (51) *Clostridium difficile* | (ATCC51695) |
| (52) *Clostridium perfringens* | (JCM1290) |
| (53) *Eggerthella lenta* | (JCM10763) |
| (54) *Fusobacterium necrophorum* | (JCM3718) |
| (55) *Fusobacterium nucleatum* | (ATCC25586) |
| (56) *Lactobacillus acidophilus* | (ATCC4356) |
| (57) *Anaerococcus prevotii* | (JCM6490) |
| (58) *Peptoniphilus asaccharolyticus* | (JCM8143) |
| (59) *Porphyromonas asaccharolytica* | (JCM6326) |
| (60) *Porphyromonas gingivalis* | (JCM8525) |
| (61) *Prevotella denticola* | (ATCC38184) |
| (62) *Propionibacterium acnes* | (JCM6473) |

(The deposition numbers of the bacterial species obtained are shown in the respective parentheses on the right side in the above.)

The present invention provides an oligonucleotide probe for identifying an infectious disease pathogenic bacterium (hereinafter, simply referred to as a probe). The use of such a probe allows the detection of the following bacterium which will cause inflammation by infection.

Bacterial Name

*Peptoniphilus asaccharolyticus*

That is, the probe of the present invention can detect the 16S rRNA gene sequence among genes of the above-mentioned bacterium, having the following sequences:

(A) a probe having a base sequence represented by GAG-TACGTGCGCAAGCATGAAACT (SEQ ID NO. 55);

(B) a probe having a complementary sequence of the base sequence represented by SEQ ID NO. 55;

(C) a probe having a modified sequence obtained by base deletion, substitution, or addition on the base sequence represented by SEQ ID NO. 55 as far as it retains the function of a probe for detecting the gene of *Peptoniphilus asaccharolyticus*; and (D) a probe having a modified sequence obtained by base deletion, substitution, or addition on the complementary sequence of the base sequence represented by SEQ ID NO. 55 as far as it retains the function of a probe for detecting the gene of *Peptoniphilus asaccharolyticus*.

The above-mentioned modified sequences may include any variation as far as it does not impair the probe's function, or any variation as far as it hybridizes with a nucleic acid sequence of interest as a detection target. Above all, it is desirable to include any variation as far as it can hybridize with a nucleic acid sequence of interest as a detection target under stringent conditions. Preferable hybridization conditions confining the variation include those represented in examples as described below. Here, the term "detection target" used herein may be one included in a sample to be used in hybridization, which may be a unique base sequence to the infectious disease pathogenic bacterium, or may be a complementary sequence to the unique sequence. Further, the variation may be a modified sequence obtained by deletion, substitution, or addition of at least one base as far as it retains a function as the probe.

The functions of those probes significantly depend on the specificity of each probe sequence corresponding to the target nucleic acid sequence of interest. The specificity of a probe sequence can be evaluated from the degree of coincidence of bases with the target nucleic acid sequence and the melting temperature between the target nucleic acid sequence and the probe sequence. Further, when a plurality of probes constitute a probe set, the variance of melting temperatures among the probes may affect the performance of the probe set.

For designing a probe sequence, a region showing a high specificity to a specific bacterial species of interest regardless of any differences in strain is selected. The region contains three or more bases which are not coincident with corresponding bases in the sequences of any other bacterial species. The probe sequence is designed so that the melting temperature between the probe sequence and the corresponding sequence of the specific bacterial species of interest will differ by 10° C. or more from the melting temperatures between the probe sequence and the corresponding sequences of any other bacterial species. Further, one or more bases can be deleted or added so that the respective probes immobilized on a single carrier may have melting temperatures within a predetermined range.

The inventors of the present invention found out by experiments that the hybridization intensity of a probe will not be significantly attenuated if 80% or more of the base sequence is consecutively conserved. It can therefore be concluded, from the finding, such that any sequences modified from the probe sequences disclosed in the specification will have a sufficient probe function if 80% or more of the base sequence of the probe is consecutively conserved.

Those probe sequences are only specific to the DNA sequence coding for the 16S rRNA of the above-mentioned bacterium, so sufficient hybridization sensitivity to the sequence will be expected even under stringent conditions. In addition, any of those probe sequences forms a stable hybridized product through a hybridization reaction thereof with a target analyte even when the probe sequences are immobilized on a carrier, which is designed to produce an excellent result.

Further, a probe-immobilized carrier (e.g., DNA chip), on which the probe for detecting the infectious disease pathogenic bacterium of the present invention, can be obtained by supplying the probe on a predetermined position on the carrier and immobilizing the probe thereon. Various methods can be used for supplying the probe to the carrier. Among them, for example, a method, which can be suitably used, is to keep a surface state capable of immobilizing the probe on the carrier through a chemical bonding (e.g., covalent bonding) and a liquid containing the probe is then provided on a predetermined position by an inkjet method. Such a method allows the probe to be hardly detached from the carrier and exerts an additional effect of improving the sensitivity. In other words, when a stamping method conventionally used and called the Stanford method is employed to make a DNA chip, the resultant DNA chip has a disadvantage such that the applied DNA tends to be peeled off. Another one of the methods of forming DNA chips is to carry out the arrangement of probes by the synthesis of DNA on the surface of a carrier (e.g., DNA chip from Affymetrix Co., Ltd.). In such a method of synthesizing probes on a carrier, it is difficult to make equal the amount of synthesized DNA for each probe sequence. Thus, the amount of immobilized probe per immobilization area (spot) for each probe tends to vary considerably. Such variations in amounts of the respective immobilized probes may cause incorrect evaluation on the results of the detection with those probes. Based on this fact, the probe carrier of the present invention is preferably prepared using the above-mentioned inkjet method. The inkjet method as described above has an advantage such that the probe can be stably immobilized on the carrier and hardly detaching from the carrier to efficiently provide a probe carrier which can carry out detection with high sensitivity and high accuracy.

Hereinafter, preferred embodiments of the present invention will be described in detail.

Test objects to be tested using probe carriers (e.g., DNA chips) in which the probes of the present invention are immobilized on carriers include those originated from humans and animals such as domestic animals. For example, a test object is any of those which may contain bacteria, including: any body fluids such as blood, cerebrospinal fluid, expectorated sputum, gastric juice, vaginal discharge, and oral mucosal fluid; and excretions such as urine and feces. All media, which can be contaminated with bacteria, can be also subjected to a test using a DNA chip. Such media include: food, drink water and water in the natural environment such as hot spring water, which may cause food poisoning by contamination; filters of air cleaners and the like; and so on. Animals and plants, which should be quarantined in import/export, are also used as analytes of interest.

When the sample as described above can be directly used in reaction with the DNA chip, it is used as an analyte to react with the DNA chip and the result of the reaction is then analyzed. Alternatively, when the sample cannot be directly reacted with the DNA chip, the sample was subjected to extraction, purification, and other procedures for obtaining a target substance if required and then provided as an analyte to carry out a reaction with the DNA chip. For instance, when the sample contains a target nucleic acid, an extract, which may be assumed to contain such a target nucleic acid, is prepared from a sample, and then washed, diluted, or the like to obtain an analyte solution followed by reaction with the DNA chip. Further, as a target nucleic acid is included in an analyte obtained by carrying out various amplification procedures such as PCR amplification, the target nucleic acid may be amplified and then reacted with a DNA chip. Such analytes of amplified nucleic acids include the following ones:

(a) An amplified analyte prepared by using a PCR-reaction primer designed for detecting 16S rRNA gene.

(b) An amplified analyte prepared by an additional PCR reaction or the like from a PCR-amplified product.

(c) An analyte prepared by an amplification method other than PCR.

(d) An analyte labeled for visualization by any of various labeling methods.

Further, a carrier used for preparing a probe-immobilized carrier, such as a DNA chip, may be any of those that satisfy the property of carrying out a solid phase/liquid phase reaction of interest. Examples of the carrier include: flat substrates such as a glass substrate, a plastic substrate, and a silicon wafer; a three-dimensional structure having an irregular surface; and a spherical body such as a bead, and rod-, cord-, and thread-shaped structures. The surface of the carrier may be processed such that a probe can be immobilized thereon. Especially, a carrier prepared by introducing a functional group to its surface to enable chemical reaction has a preferable form from the viewpoint of reproducibility because the probe is stably bonded in the process of hybridization reaction.

Various methods can be employed for the immobilization of probes. An example of such a method is to use a combination of a maleimide group and a thiol (—SH) group. In this method, a thiol (—SH) group is bonded to the terminal of a probe, and a process is executed in advance to make the carrier (solid) surface have a maleimide group. Accordingly, the thiol group of the probe supplied to the carrier surface reacts with the maleimide group on the carrier surface to form a covalent bond, whereby the probe is immobilized.

Introduction of the maleimide group can utilize a process of firstly allowing a reaction between a glass substrate and an aminosilane coupling agent and then introducing an maleimide group onto the glass substrate by a reaction of the amino group with an EMCS reagent (N-(6-maleimidocaproyloxy) succinimide, available from Dojindo). Introduction of the thiol group to a DNA can be carried out using 5'-Thiol-Modifier C6 (available from Glen Research) when the DNA is synthesized by an automatic DNA synthesizer.

Instead of the above-described combination of a thiol group and a maleimide group, a combination of, e.g., an epoxy group (on the solid phase) and an amino group (nucleic acid probe terminal), can also be used as a combination of functional groups to be used for immobilization. Surface treatments using various kinds of silane coupling agents are also effective. A probe in which a functional group which can react with a functional group introduced by a silane coupling agent is introduced is used. A method of applying a resin having a functional group can also be used.

The detection of the gene of the infectious disease pathogenic bacterium by using the probe-immobilized carrier of the present invention can be carried out by a genetic testing method including the steps of:

(i) reacting an analyte with a probe-immobilized carrier on which the probe of the present invention is immobilized;

(ii) detecting the presence or absence of the reaction of a nucleic acid in the analyte with the probe on the probe-immobilized carrier, or detecting the strength of the reaction of a nucleic acid in the analyte with the probe on the probe-immobilized carrier; and (iii) specifying the probe having reacted with the nucleic acid in the analyte when the reaction of the probe with the nucleic acid in the analyte is detected and specifying the gene of the infectious disease pathogenic bacterium in the analyte based on the nucleic acid sequence of the probe.

The probe to be immobilized on the probe-immobilized carrier is at least one of the above-mentioned items (A) to (D). On the carrier, other probes (those for detecting bacterial species other than *Peptoniphilus asaccharolyticus*) may be immobilized depending on the purpose of test. In this case, the other probes may be those capable of detecting the bacterial species other than *Peptoniphilus asaccharolyticus* without causing cross contamination and the use of such probes allows simultaneous detection of a plurality of bacterial species with high accuracy.

Further, as described above, when the 16S rRNA gene sequence of an infectious disease pathogenic bacterium in the analyte is amplified by PCR and provided as a sample to be reacted with a probe carrier, a primer set for detecting the infectious disease pathogenic bacterium can be used. The primer set suitably includes at least one selected from oligonucleotides represented in the following items (1) to (21) and at least one selected from oligonucleotides represented in the following items (22) to (28), more suitably includes all the oligonucleotides represented in the following items (1) to (28):

(1) an oligonucleotide having a base sequence of

5' gcggcgtgcctaatacatgcaag 3';  (SEQ ID NO: 1)

(2) an oligonucleotide having a base sequence of

5' gcggcaggcctaacacatgcaag 3';  (SEQ ID NO: 2)

(3) an oligonucleotide having a base sequence of

5' gcggcaggcttaacacatgcaag 3';  (SEQ ID NO: 3)

(4) an oligonucleotide having a base sequence of

5' gcggtaggcctaacacatgcaag 3';  (SEQ ID NO: 4)

(5) an oligonucleotide having a base sequence of

5' gcggcgtgcttaacacatgcaag 3';  (SEQ ID NO: 5)

(6) an oligonucleotide having a base sequence of

5' gcgggatgccttacacatgcaag 3';  (SEQ ID NO: 6)

(7) an oligonucleotide having a base sequence of

5' gcggcatgccttacacatgcaag 3';  (SEQ ID NO: 7)

(8) an ligonucleotide having a base sequence of

5' gcggcatgcttaacacatgcaag 3';  (SEQ ID NO: 8)

(9) an oligonucleotide having a base sequence of

5' gcggcgtgcttaatacatgcaag 3';  (SEQ ID NO: 9)

(10) an oligonucleotide having a base sequence of

5' gcggcaggcctaatacatgcaag 3';  (SEQ ID NO: 10)

(11) an oligonucleotide having a base sequence of

5' gcgggatgctttacacatgcaag 3';  (SEQ ID NO: 11)

(12) an oligonucleotide having a base sequence of

5' gcggcgtgcctaacacatgcaag 3';  (SEQ ID NO: 12)

(13) an oligonucleotide having a base sequence of

5' gcggcgtgcataacacatgcaag 3';  (SEQ ID NO: 13)

(14) an oligonucleotide having a base sequence of

5' gcggcatgcctaacacatgcaag 3';  (SEQ ID NO: 14)

(15) an oligonucleotide having a base sequence of

5' gcggcgcgcctaacacatgcaag 3';  (SEQ ID NO: 15)

(16) an oligonucleotide having a base sequence of

5' gcggcgcgcttaacacatgcaag 3';  (SEQ ID NO: 16)

(17) an oligonucleotide having a base sequence of

5' gcgtcatgcctaacacatgcaag 3';  (SEQ ID NO: 17)

(18) an oligonucleotide having a base sequence of

5' gcgataggcttaacacatgcaag 3';  (SEQ ID NO: 18)

(19) an oligonucleotide having a base sequence of

5' gcgacaggcttaacacatgcaag 3';  (SEQ ID NO: 19)

(20) an oligonucleotide having a base sequence of

5' gctacaggcttaacacatgcaag 3';  (SEQ ID NO: 20)

(21) an oligonucleotide having a base sequence of

5' acagaatgcttaacacatgcaag 3';  (SEQ ID NO: 21)

(22) an oligonucleotide having a base sequence of

5' atccagccgcaccttccgatac 3';   (SEQ ID NO: 22)

(23) an oligonucleotide having a base sequence of

5' atccaaccgcaggttcccctac 3';   (SEQ ID NO: 23)

(24) an oligonucleotide having a base sequence of

```
5' atccagccgcaggttcccctac 3';    (SEQ ID NO: 24)
```

(25) an oligonucleotide having a base sequence of

```
5' atccagccgcaccttccggtac 3';    (SEQ ID NO: 25)
```

(26) an oligonucleotide having a base sequence of

```
5' atccagcgccaggttcccctag 3';    (SEQ ID NO: 26)
```

(27) an oligonucleotide having a base sequence of

```
5' atccagccgcaggttctcctac 3';    (SEQ ID NO: 27)
```
and

(28) an oligonucleotide having a base sequence of

```
5' atccagccgcacgttcccgtac 3'.    (SEQ ID NO: 28)
```

Among them, a primer designed for allowing the amplification of *Peptoniphilus asaccharolyticus* is a primer set including at least one of

(15) an oligonucleotide having a base sequence of 5' gcggcgcgcctaacacatgcaag 3' (SEQ ID NO: 15) and

(16) an oligonucleotide having a base sequence of 5' gcggcgcgcgottaacacatgoaag 3' (SEQ ID NO: 16); and at least one of

(22) an oligonucleotide having a base sequence of 5' atccagccgcaccttccgatac 3' (SEQ ID NO: 22) and

(25) an oligonucleotide having a base sequence of 5' atccagccgcaccttccggtac 3' (SEQ ID NO: 25).

For detecting *Peptoniphilus asaccharolyticus*, at least such a primer may be included.

The utilities of the respective primers (1) to (28) for amplification of *Peptoniphilus asaccharolyticus* (JCM8143) can be evaluated and confirmed by comparing each sequence of SEQ ID NOS. 1 to 28 with a DNA sequence including the 16S rRNA coding region of *Peptoniphilus asaccharolyticus* (SEQ ID NO. 68).

A kit for detecting the infectious disease pathogenic bacterium can be constructed using at least a probe as described above and a reagent for detecting a reaction of the probe with a nucleic acid in an analyte. The probe in the kit can preferably be provided as a probe-immobilized carrier as described above. Further, the detection reagent may contain a label to detect the reaction or a primer for carrying out amplification as a pre-treatment.

EXAMPLES

Hereinafter, the present invention will be described in more detail with reference to examples using probes for detecting an infectious disease pathogenic bacterium to detect *Peptoniphilus asaccharolyticus*.

Example 1

In this example, microorganism detection using 2-step PCR will be described.
1. Preparation of Probe DNA
Nucleic acid sequences shown in Table 1 were designed as probes to be used for detection of *Peptoniphilus asaccharolyticus*. Specifically, the following probe base sequences were selected from the genome part coding for the 16s rRNA gene of *Peptoniphilus asaccharolyticus*. These probe base sequences were designed such that they could have an extremely high specificity to the bacterium, and a sufficient hybridization sensitivity could be expected without variance for the respective probe base sequences. The probe base sequences need not always completely match with those shown in Table 1. Probe base sequences having base lengths of 20 to 30, including the probe base sequences shown in Table 1, are also included in the probe base sequence shown in Table 1.

TABLE 1

| Name of microorganism | Probe No. | SEQ ID NO. | Sequence |
|---|---|---|---|
| *Peptoniphilus asaccharolyticus* | PA1 | 55 | 5' GAGTACGTGCGCAAGCATGAAACT 3' |

For each probe shown in Table 1, a thiol group was introduced, as a functional group to immobilize the probe on a DNA chip, to the 5' terminal of the nucleic acid after synthesis in accordance with a conventional method. After introduction of the functional group, purification and freeze-drying were executed. The freeze-dried probes for internal standard were stored in a freezer at −30° C.
2. Preparation of PCR Primers
2-1. Preparation of PCR Primers for Analyte Amplification
As 16S rRNA gene (target gene) amplification PCR primers for pathogenic bacterium detection, nucleic acid sequences shown in Table 2 below were designed. Specifically, primer sets which specifically amplify the genome parts coding the 16S rRNAs, i.e., primers for which the specific melting points were made uniform as far as possible at the two end portions of the 16S rRNA coding region of a base length of 1,400 to 1,700 were designed. In order to simultaneously amplify a plurality of different bacterial species listed in the following items (1) to (62), mutants, or a plurality of 16S rRNA genes on genomes, a plurality of kinds of primers were designed. Note that a primer set is not limited to the primer sets shown in Table 2 as far as the primer set is available in common to amplify almost the entire lengths of the 16S rRNA genes of the pathogenic bacteria.

TABLE 2

| Primer No | SEQ ID NO. | Sequence |
|---|---|---|
| F01 | 1 | 5' GCGGCGTGCCTAATACATGCAAG 3' |
| F02 | 2 | 5' GCGGCAGGCCTAACACATGCAAG 3' |
| F03 | 3 | 5' GCGGCAGGCTTAACACATGCAAG 3' |
| F04 | 4 | 5' GCGGTAGGCCTAACACATGCAAG 3' |
| F05 | 5 | 5' GCGGCGTGCTTAACACATGCAAG 3' |
| F06 | 6 | 5' GCGGGATGCCTTACACATGCAAG 3' |
| F07 | 7 | 5' GCGGCATGCCTTACACATGCAAG 3' |
| F08 | 8 | 5' GCGGCATGCTTAACACATGCAAG 3' |
| F09 | 9 | 5' GCGGCGTGCTTAATACATGCAAG 3' |
| F10 | 10 | 5' GCGGCAGGCCTAATACATGCAAG 3' |
| F11 | 11 | 5' GCGGGATGCTTTACACATGCAAG 3' |

TABLE 2-continued

| Primer No | SEQ ID NO. | Sequence |
|---|---|---|
| F12 | 12 | 5' GCGGCGTGCCTAACACATGCAAG 3' |
| F13 | 13 | 5' GCGGCGTGCATAACACATGCAAG 3' |
| F14 | 14 | 5' GCGGCATGCCTAACACATGCAAG 3' |
| F15 | 15 | 5' GCGGCGCGCCTAACACATGCAAG 3' |
| F16 | 16 | 5' GCGGCGCGCTTAACACATGCAAG 3' |
| F17 | 17 | 5' GCGTCATGCCTAACACATGCAAG 3' |
| F18 | 18 | 5' GCGATAGGCTTAACACATGCAAG 3' |
| F19 | 19 | 5' GCGACAGGCTTAACACATGCAAG 3' |
| F20 | 20 | 5' GCTACAGGCTTAACACATGCAAG 3' |
| F21 | 21 | 5' ACAGAATGCTTAACACATGCAAG 3' |
| R01 | 22 | 5' ATCCAGCCGCACCTTCCGATAC 3' |
| R02 | 23 | 5' ATCCAACCGCAGGTTCCCCTAC 3' |
| R03 | 24 | 5' ATCCAGCCGCAGGTTCCCCTAC 3' |
| R04 | 25 | 5' ATCCAGCCGCACCTTCCGGTAC 3' |
| R05 | 26 | 5' ATCCAGCCGCAGGTTCCCCTAG 3' |
| R06 | 27 | 5' ATCCAGCCGCAGGTTCTCCTAC 3' |
| R07 | 28 | 5' ATCCAGCCGCACGTTCCCGTAC 3' |

(1) *Staphylococcus aureus*
(2) *Staphylococcus epidermidis*
(3) *Escherichia coil*
(4) *Klebsiella pneumoniae*
(5) *Pseudomonas aeruginosa*
(6) *Serratia marcescens*
(7) *Streptococcus pneumoniae*
(8) *Haemophilus influenzae*
(9) *Enterobacter cloacae*
(10) *Enterococcus faecalis*
(11) *Staphylococcus haemolyticus*
(12) *Staphylococcus hominis*
(13) *Staphylococcus saprophyticus*
(14) *Streptococcus agalactiae*
(15) *Streptococcus mutans*
(16) *Streptococcus pyogenes*
(17) *Streptococcus sanguinis*
(18) *Enterococcus avium*
(19) *Enterococcus faecium*
(20) *Pseudomonas fluorescens*
(21) *Pseudomonas putida*
(22) *Burkholderia cepacia*
(23) *Stenotrophomonas maltophilia*
(24) *Acinetobacter baumannii*
(25) *Acinetobacter calcoaceticus*
(26) *Achromobacter xylosoxidans*
(27) *Vibrio vulnificus*
(28) *Salmonella choleraesuis*
(29) *Citrobacter freundii*
(30) *Klebsiella oxytoca*
(31) *Enterobacter aerogenes*
(32) *Hafnia alvei*
(33) *Serratia liquefaciens*
(34) *Proteus mirabilis*
(35) *Proteus vulgaris*
(36) *Morganella morganii*
(37) *Providencia rettgeri*
(38) *Aeromonas hydrophila*
(39) *Aeromonas sobria*
(40) *Gardnerella vaginalis*
(41) *Corynebacterium diphtheriae*
(42) *Legionella pneumophila*
(43) *Bacillus cereus*
(44) *Bacillus subtilis*
(45) *Mycobacterium kansasii*
(46) *Mycobacterium intracellulare*
(47) *Mycobacterium chelonae*
(48) *Nocardia asteroides*
(49) *Bacteroides fragilis*
(50) *Bacteroides thetaiotaomicron*
(51) *Clostridium difficile*
(52) *Clostridium perfringens*
(53) *Eggerthella lenta*
(54) *Fusobacterium necrophorum*
(55) *Fusobacterium nucleatum*
(56) *Lactobacillus acidophilus*
(57) *Anaerococcus prevotii*
(58) *Peptoniphilus asaccharolyticus*
(59) *Porphyromonas asaccharolytica*
(60) *Porphyromonas gingivalis*
(61) *Prevotella denticola*
(62) *Propionibacterium acnes*

The primers shown in Table 2 were purified by high performance liquid chromatography (HPLC) after synthesis. The twenty-one forward primers and the seven reverse primers were mixed and dissolved in a TE buffer solution such that each primer concentration had an ultimate concentration of 10 pmol/µl.

2-2. Preparation of Labeling PCR Primers

In a manner similar to the above-mentioned analyte amplification primers, oligonucleotides having sequences as shown in Table 3 below were employed as primers for labeling.

TABLE 3

| Primer No | SEQ ID NO. | Sequence |
|---|---|---|
| Cy3R9-1 | 29 | 5' TACCTTGTTACGACTTCACCCCA 3' |
| Cy3R9-2 | 30 | 5' TACCTTGTTACGACTTCGTCCCA 3' |
| Cy3R9-3 | 31 | 5' TACCTTGTTACGACTTAGTCCCA 3' |
| Cy3R9-4 | 32 | 5' TACCTTGTTACGACTTAGCCCCA 3' |
| Cy3R9-5 | 33 | 5' TACCTTGTTACGACTTAGTCCTA 3' |
| Cy3R9-6 | 34 | 5' TACCTTGTTACGACTTAGCCCTA 3' |

The primers shown in Table 3 were labeled with a fluorescent dye, Cy3. The primers were purified by high performance liquid chromatography (HPLC) after synthesis. The six labeled primers were mixed and dissolved in a TE buffer solution such that each primer concentration had an ultimate concentration of 10 µmol/µl.

3. Extraction of Genome DNA (Model Analyte) of *Peptoniphilus asaccharolyticus*

3-1. Microbial Culture & Genome DNA Extraction

First, *Peptoniphilus asaccharolyticus* (JCM8143) was cultured in accordance with the conventional method. This microbial culture medium was subjected to the extraction and purification of genome DNA by using a nucleic acid purification kit (FastPrep FP100A FastDNA Kit, manufactured by Funakoshi Co., Ltd.).

3-2. Test of Collected Genome DNA

The collected genome DNA of the microorganism (*Peptoniphilus asaccharolyticus*) was subjected to agarose electrophoresis and 260/280-nm absorbance determination in accordance with the conventional method. Thus, the quality (the admixture amount of low molecular nucleic acid and the degree of decomposition) and the collection amount were tested. In this example, about 10 μg of the genome DNA was collected. No degradation of genome DNA or contamination of rRNA was observed. The collected genome DNA was dissolved in a TE buffer solution at an ultimate concentration of 50 ng/μl and used in the following experiments.

4. Preparation of DNA Chip 4-1. Cleaning of Glass Substrate

A glass substrate (size: 25 mm×75 mm×1 mm, available from Iiyama Precision Glass) made of synthetic quartz was placed in a heat- and alkali-resisting rack and dipped in a cleaning solution for ultrasonic cleaning, which was adjusted to have a predetermined concentration. The glass substrate was kept dipped in the cleaning solution for a night and cleaned by ultrasonic cleaning for 20 min. The substrate was picked up, lightly rinsed with pure water, and cleaned by ultrasonic cleaning in ultrapure water for 20 min. The substrate was dipped in a 1N aqueous sodium hydroxide solution heated to 80° C. for 10 min. Pure water cleaning and ultrapure water cleaning were executed again. A quartz glass substrate for a DNA chip was thus prepared.

4-2. Surface Treatment

A silane coupling agent KBM-603 (available from Shin-Etsu Silicone) was dissolved in pure water at a concentration of 1% by weight (wt %) and stirred at room temperature for 2 hrs. The cleaned glass substrate was dipped in the aqueous solution of the silane coupling agent and left stand still at room temperature for 20 min. The glass substrate was picked up. The surface thereof was lightly rinsed with pure water and dried by spraying nitrogen gas to both surfaces of the substrate. The dried substrate was baked in an oven at 120° C. for 1 hr to complete the coupling agent treatment, whereby an amino group was introduced to the substrate surface. Next, N-maleimidocaproyloxy succinimido (abbreviated as EMCS hereinafter) was dissolved in a 1:1 (volume ratio) solvent mixture of dimethyl sulfoxide and ethanol to obtain an ultimate concentration of 0.3 mg/ml. As a result, an EMCS solution was prepared. Here, EMCS is N-(6-maleimidocaproyloxy)succinimido available from Dojindo.

The baked glass substrate was left stand and cooled and dipped in the prepared EMCS solution at room temperature for 2 hrs. By this treatment, the amino group introduced to the surface of the substrate by the silane coupling agent reacted with the succinimide group in the EMCS to introduce the maleimide group to the surface of the glass substrate. The glass substrate picked up from the EMCS solution was cleaned by using the above-described solvent mixture in which the EMCS was dissolved. The glass substrate was further cleaned by ethanol and dried in a nitrogen gas atmosphere.

4-3. Probe DNA

The microorganism detection probe prepared in the stage 1 (Preparation of Probe DNA) of Example 1 was dissolved in pure water. The solution was dispensed such that the ultimate concentration (at ink dissolution) became 10 μM. Then, the solution was freeze-dried to remove water.

4-4. DNA Discharge by BJ Printer and Bonding to Substrate

An aqueous solution containing 7.5-wt % glycerin, 7.5-wt % thiodiglycol, 7.5-wt % urea, and 1.0-wt % Acetylenol EH (available from Kawaken Fine Chemicals) was prepared. Each of the two probes (Table 1) prepared in advance was dissolved in the solvent mixture at a specific concentration. An ink tank for an inkjet printer (trade name: BJF-850, available from Canon) is filled with the resultant DNA solution and attached to the printhead.

The inkjet printer used here was modified in advance to allow printing on a flat plate. When a printing pattern is input in accordance with a predetermined file creation method, an about 5-picoliter of a DNA solution can be spotted at a pitch of about 120 μm.

The printing operation was executed for one glass substrate by using the modified inkjet printer to prepare an array. After confirming that printing was reliably executed, the glass substrate was left stand still in a humidified chamber for 30 min to make the maleimide group on the glass substrate surface react with the thiol group at the nucleic acid probe terminal.

4-5. Cleaning

After reaction for 30 min, the DNA solution remaining on the surface was cleaned by using a 10-mM phosphate buffer (pH 7.0) *containing* 100-mM NaCl, thereby obtaining a DNA chip in which single-stranded DNAs were immobilized on the glass substrate surface.

5. Amplification and Labeling of Analyte 5-1. Amplification of Analyte: 1st PCR

The amplification reaction (1st PCR) and the labeling reaction (2nd PCR) of a microbial gene to be provided as an analyte are shown in Table 4 below.

TABLE 4

| AmpliTaq Gold LD (5.0 U/μL) | 0.5 μL (2.5 unit/tube) |
|---|---|
| Primer mix <FR21x7> | 2.0 μL |
| Forward primer (x21 [0.625 μM/each]) | (final 1.25 pmol each/tube) |
| Reverse primer (x07 [1.875 μM/each]) | (final 3.75 pmol each/tube) |
| 10× PCR buffer | 5.0 μL (final 1x conc.) |
| $MgCl_2$ (25 mM) | 8.0 μL (final 4.0 mM) |
| dNTPmix (2.5 mM/each) | 4.0 μL (final 200 μM each) |
| Template | variable |
| $H_2O$ | up to 50 μL |
| Total | 50 μL |

Amplification reaction of the reaction solution having the above-mentioned composition was carried out using a commercially available thermal cycler in accordance with the protocol illustrated in FIG. 1. After the end of reaction, the primer was purified using a purification column (QIAquick PCR Purification Kit available from QIAGEN). Subsequently, the quantitative assay of the amplified product was carried out.

5-2. Labeling Reaction: 2nd PCR

Amplification reaction of the reaction solution having the composition shown in Table 5 was carried out using a commercially available thermal cycler in accordance with the protocol illustrated in FIG. 2.

TABLE 5

| Premix Taq (Ex Taq Version) | 25 μL |
|---|---|
| Cy3-labeled reverse primer mix | 0.83 μL |
| Cy3R9 mix (x06[10 μM/each]) | (final 8.3 pmol each/tube) |
| Template | variable (final 30 ng/tube) |
| $H_2O$ | up to 50 μL |
| Total | 50 μL |

After the end of reaction, the primer was purified using a purification column (QIAquick PCR Purification Kit available from QIAGEN) to obtain a labeled analyte.

6. Hybridization

Detection reaction was performed using the DNA chip prepared in the stage 4 (Preparation of DNA Chip) and the labeled analyte prepared in the stage 5 (Amplification and Labeling of Analyte).

6-1. Blocking of DNA Chip

Bovine serum albumin (BSA, Fraction V: available from Sigma) was dissolved in a 100-mM NaCl/10-mM phosphate buffer such that a 1 wt % solution was obtained. Then, the DNA chip prepared in the stage 4 (Preparation of DNA Chip) was dipped in the solution at room temperature for 2 hrs to execute blocking. After the end of blocking, the chip was cleaned using a washing solution as described below, rinsed with pure water and hydro-extracted by a spin dryer. The washing solution: 2×SSC solution (NaCl 300 mM, sodium citrate (trisodium citrate dihydrate, $C_6H_5Na_3.2H_2O$) 30 mM, pH 7.0) containing 0.1-wt % sodium dodecyl sulfate (SDS)

6-2. Hybridization

The hydro-extracted DNA chip was placed in a hybridization apparatus (Hybridization Station available from Genomic Solutions Inc). Hybridization reaction was carried out in a hybridization solution under conditions as described below.

6-3. Hybridization Solution

6×SSPE/10% formamide/target (all 2nd PCR products)/0.05 wt % (6×SSPE: NaCl 900 mM, $NaH_2PO_4H_2O$ 50 mM, EDTA 6 mM, pH, 7.4)

6-4. Hybridization Conditions

65° C. for 3 min, 55° C. for 4 hrs, washing with 2×SSC/0.1% SDS at 50° C., washing with 2×SSC/0.1% SDS at 20° C. (rinse with $H_2O$: manual), and spin dry.

7. Microorganism Genome Detection (Fluorometry)

The DNA chip after the end of hybridization reaction was subjected to fluorometry with a DNA chip fluorescent detector (GenePix 4000B available from Axon). As a result, *Peptoniphilus asaccharolyticus* was able to be detected with a sufficient signal at a high reproducibility. The results of fluorometry are shown in Table 6 below.

TABLE 6

| Name of Probe | Fluorescence intensity | S/N |
|---|---|---|
| PA1 | 1185.6 | 9.6 |

8. Hybridization with Other Bacterial Species

For proving the fact that the probe sets shown in Table 1 can be specifically hybridized only with *Peptoniphilus asaccharolyticus*, the results of hybridization reaction with *Anaerococcus prevotii* (JCM6490) are shown in Table 7 below.

TABLE 7

| Name of Probe | Fluorescence intensity | S/N |
|---|---|---|
| PA1 | 123.6 | 1.0 |

9. Results

As is evident from the above description, a DNA chip was prepared such that a probe set, which was able to detect only *Peptoniphilus asaccharolyticus* in a specific manner, was immobilized. Further, the use of such a DNA chip allowed the identification of an infectious disease pathogenic bacterium, so the problems of the DNA probe derived from a microorganism was able to be solved. In other words, the oligonucleotide probe can be chemically produced in large amounts, while the purification or concentration thereof can be controlled. In addition, for classification of microbial species, a probe set capable of collectively detecting bacterial strains of the same species and differentially detecting them from bacteria of other species, was able to be provided.

Further, in addition to *Anaerococcus prevotii* as described above, hybridization reaction was carried out on each of nucleic acids extracted from the bacteria represented in the above-mentioned items (1) to (62). The results thereof confirmed that no substantial reaction was observed with respect to each of those bacteria in a manner similar to that of *Anaerococcus prevotii*, except of *Peptoniphilus asaccharolyticus*.

The bacteria represented in the above-mentioned items (1) to (62) are pathogenic bacteria for septicemia, and they cover almost all of the pathogenic bacteria ever detected in human blood. Therefore, by using the primer of the present embodiment, the nucleic acid of an infectious disease pathogenic bacterium in blood can be extracted and then reacted with the probe of the present invention, whereby substantially accurate identification of *Peptoniphilus asaccharolyticus* can be performed.

Further, according to the above-mentioned example, the presence of an infectious disease pathogenic bacterium can be efficiently determined with high accuracy by completely detecting the 16S rRNA gene from the gene of the infectious disease pathogenic bacterium.

Example 2

Preparation of DNA Chip by which Various Bacterial Species can be Simultaneously Determined In a manner similar to the stage 1 (Preparation of Probe DNA) of Example 1, probes having base sequences as shown in Table 8 below were prepared.

TABLE 8

| Bacterial species of interest | Probe sequence (5'→3') | SEQ ID NO. |
|---|---|---|
| Anaerococcus prevotii | TCATCTTGAGGTATGGAAGGGAAAGTGG | 35 |
| | GTGTTAGGTGTCTGGAATAATCTGGGTG | 36 |
| | ACCAAGTCTTGACATATTACGGCGG | 37 |
| Bacteroides fragilis | AAGGATTCCGGTAAAGGATGGGGATG | 38 |
| | TGGAAACATGTCAGTGAGCAATCACC | 39 |
| Bacteroides thetaiotaomicron | AAGAATTTCGGTTATCGATGGGGATGC | 40 |
| | AAGTTTTCCACGTGTGGAATTTTGTATGT | 41 |
| | AAGGCAGCTACCTGGTGACAGGAT | 42 |
| Clostridium difficile | AATATCAAAGGTGAGCCAGTACAGGATGGA | 43 |
| | CCGTAGTAAGCTCTTGAAACTGGGAGAC | 44 |
| | TCCCAATGACATCTCCTTAATCGGAGAG | 45 |
| Clostridium perfringens | AACCAAAGGAGCAATCCGCTATGAGAT | 46 |
| | GAGCGTAGGCGGATGATTAAGTGGG | 47 |
| | CCCTTGCATTACTCTTAATCGAGGAAATC | 48 |
| Eggerthella lenta | GGAAAGCCCAGACGGCAAGGGA | 49 |
| | CCTCTCAAGCGGGATCTCTAATCCGA | 50 |
| | TGCCCCATGTTGCCAGCATTAGG | 51 |
| Fusobacterium necrophorum | TTTTCGCATGGAGGAATCATGAAAGCTA | 52 |
| | AGATGCGCCGGTGCCCTTTCG | 53 |
| | AGTCGGGAAGAAGTCAGTGACGGTAC | 54 |

TABLE 8-continued

| Bacterial species of interest | Probe sequence (5'→3') | SEQ ID NO. |
|---|---|---|
| Peptoniphilus asaccharolyticus | GAGTACGTGCGCAAGCATGAAACT | 55 |
| Porphyromonas asaccharolytica | GAAGACTGCCCGCAAGGGTTGTAA | 56 |
|  | GTGTACTGGAGGTACGTGGAACGTG | 57 |
|  | GCATGAGGCTGAGAGGTCTCTTCC | 58 |
| Porphyromonas gingivalis | TTATAGCTGTAAGATAGGCATGCGTCCC | 59 |
|  | AACGGGCGATACGAGTATTGCATTGA | 60 |
|  | ATATACCGTCAAGCTTCCACAGCGA | 61 |
| Enterococcus avium | TTTGAAAGGCGCTTTTGCGTCACTG | 62 |
|  | CAAGGATGAGAGTAGAACGTTCATCCCTTG | 63 |
|  | CAAGGATGAGAGTAGAATGTTCATCCCTTG | 64 |
| Providencia rettgeri | CCTGGGAATGGCATCTAAGACTGGTCA | 65 |
|  | GAGGAAGGCGTTGATGCTAATATCATCA | 66 |
|  | GAGCAAAGCAGGGGAACTTCGGTC | 67 |

Those probes are capable of specifically detecting certain bacterial species shown in the left column in the table just as one specific to *Peptoniphilus asaccharolyticus* of Example 1.

Further, those probes are designed such that they have the same Tm value as that of a target, the same reactivity with a non-target sequence, and the like so that the nucleic acid of the bacterial species of interest can be specifically detected under the same reaction conditions.

For the respective probes, probe solutions were prepared in a manner similar to the stage 4-3 of Example 1. Subsequently, the inkjet printer used in the stage 4-4 of Example 1 was employed to discharge each of the probe solution on the same substrate to form a plurality of DNA chips having spots of the respective probes being arranged at a pitch of about 120 μm.

One of the DNA chips was used for hybridization with the nucleic acid extracted from *Peptoniphilus asaccharolyticus* in a manner similar to the stage 6 of Example 1. As a result, the spot of the probe which specifically detected *Peptoniphilus asaccharolyticus* showed almost the equal fluorescence intensity as that of Example 1. In contrast, the spots of other probes showed extremely low fluorescence intensity.

Further, other prepared DNA chips were used for hybridization with the bacteria listed in Table 8 except of *Peptoniphilus asaccharolyticus*. As a result, the spot of *Peptoniphilus asaccharolyticus* showed extremely low fluorescence intensity, while the spot of the probe for the bacterial species of interest showed extremely high fluorescence intensity. Therefore, the DNA chip prepared in the present example was confirmed that it was able to simultaneously determine eleven bacterial species listed in Table 8 in addition to *Peptoniphilus asaccharolyticus*.

Example 3

Using the DNA chip prepared in Example 2, detection was attempted when a plurality of bacterial species was present in an analyte.

A culture medium in which *Peptoniphilus asaccharolyticus* and *Clostridium difficile* were cultured was prepared and subjected to the same treatment as that of Example 1 to react with the DNA chip.

As a result, only the spots of the probes having SEQ ID NOS. 43, 44, 45, and 55 showed high fluorescence intensity, so the coexistence of those bacteria was able to be simultaneously confirmed.

The present invention is not limited to the above-mentioned embodiments and various changes and modifications can be made within the spirit and scope of the present invention. Therefore to apprise the public of the scope of the present invention, the following claims are made.

This application claims the benefit of Japanese Patent Application No. 2006-098675, filed Mar. 31, 2006, which is hereby incorporated by reference herein in its entirety.

The invention claimed is:

1. A probe-immobilized carrier comprising:
a first probe for detecting a gene of infectious disease pathogenic bacterium, *Peptoniphilus asaccharolyticus*, the first probe consisting of the base sequence of GAG-TACGTGCGCAAGCATGAAACT (SEQ ID NO. 55) or the complementary sequence thereof, the first probe being arranged on a solid phase carrier; and
a second probe comprising any one of the base sequences of SEQ ID NOS. 35 to 54 and 56 to 67 immobilized at a position spaced from the first probe.

2. A probe-immobilized carrier according to claim 1, wherein the first probe shows a hybridization intensity weak enough to avoid cross-hybridization with the 16S rRNA coding region of any bacterium selected from *Anaerococcus prevotii*, *Bacteroides fragilis*, *Bacteroides thetaiotaomicron*, *Clostridium difficile*, *Clostridium perfringens*, *Eggerthella lento*, *Fusobacterium necrophorum*, *Porphyromonas asaccharolytica*, *Porphyromonas gingivalis*, *Enterococus avium* and *Providencia rettgeri*.

3. A probe-immobilized carrier according to claim 1, wherein the first probe shows a hybridization intensity weak enough to avoid cross-hybridization with the 16S rRNA coding region of any bacterium selected from *Staphylococcus aureus*, *Staphylococcus epidermidis*, *Escherichia coli*, *Klebsiella pneumoniae*, *Pseudomonas aeruginosa*, *Serratia marcescens*, *Streptococcus pneumoniae*, *Haemophilus influenzae*, *Enterobacter cloacae*, *Enterococcus faecalis*, *Staphylococcus haemolyticus*, *Staphylococcus hominis*, *Staphylococcus saprophyticus*, *Streptococcus agalactiae*, *Streptococcus mutans*, *Streptococcus pyogenes*, *Streptococcus sanguinis*, *Enterococcus avium*, *Enterococcus faecium*, *Pseudomonas fluorescens*, *Pseudomonas putida*, *Burkholderia cepacia*, *Stenotrophomonas maltophilia*, *Acinetobacter baumannii*, *Acinetobacter calcoaceticus*, *Achromobacter xylosoxidans*, *Vibrio vulnificus*, *Salmonella choleraesuis*, *Citrobacter freundii*, *Klebsiella oxytoca*, *Enterobacter aerogenes*, *Hafnia alvei*, *Serratia liquefaciens*, *Proteus mirabilis*, *Proteus vulgaris*, *Morganella morganii*, *Providencia rettgeri*, *Aeromonas hydrophila*, *Aeromonas sobria*, *Gardnerella vaginalis*, *Corynebacterium diphtheriae*, *Legionella pneumophila*, *Bacillus cereus*, *Bacillus subtilis*, *Mycobacterium kansasii*, *Mycobacterium intracellulare*, *Mycobacterium chelonae*, *Nocardia asteroids*, *Bacteroides fragilis*, *Bacteroides thetaiotaomicron*, *Clostridium difficile*, *Clostridium perfrigens*, *Eggerthella lenta*, *Fusobacterium necrophorum*, *Fusobacterium nucleatum*, *Lactobacillus acidophilus*, *Anaerococcus prevotii*, *Porphyromonas asaccharolytica*, *Porphyromonas gingivalis*, *Prevotella denticola*, and *Propionibacterium acnes*.

4. A kit for detecting a gene of *Peptoniphilus asaccharolyticus*, comprising:
the probe-immobilized carrier of claim 1; and
a reagent for detecting a reaction between the first probe and a target nucleic acid.

5. A kit according to claim 4, wherein the reagent comprises a primer set for amplifying the gene of *Peptoniphilus asaccharolyticus*, wherein the primer set comprises:
at least one of the oligonucleotides selected from the group consisting of:
an oligonucleotide comprising a base sequence of 5' gcggcgcgcctaacacatgcaag 3' (SEQ ID NO: 15); and
an oligonucleotide comprising a base sequence of 5' gcggcgcgcttaacacatgcaag 3' (SEQ ID NO: 16); and
at least one of the oligonucleotides selected from the group consisting of:
an oligonucleotide comprising a base sequence of 5' atccagccgcaccttccgatac 3' (SEQ ID NO: 22); and
an oligonucleotide comprising a base sequence of 5' atccagccgcaccttccggtac 3' (SEQ ID NO: 25).

6. A method of detecting a gene of *Peptoniphilus asaccharolyticus* in an analyte by using a probe-immobilized carrier, comprising the steps of:

(i) reacting the analyte with the first probe on the probe-immobilized carrier of claim 1; and (ii) detecting the presence or absence of a hybridization reaction of the first probe on the probe-immobilized carrier with a nucleic acid in the analyte, or detecting the strength of a hybridization reaction of the first probe on the probe-immobilized carrier with a nucleic acid in the analyte, wherein the presence of the hybridization reaction or the strength of the hybridization reaction indicates the presence of a gene of *Peptoniphilus asaccharolyticus* in the analyte.

7. A method according to claim 6, further comprising the step of carrying out PCR amplification of the target nucleic acid in the analyte by using a primer set, wherein the primer set comprises:

an oligonucleotide comprising a base sequence of 5' gcggcgcgcctaacacatgcaag 3' (SEQ ID NO: 15);

an oligonucleotide comprising a base sequence of 5' gcggcgcgcttaacacatgcaag 3' (SEQ ID NO: 16); and at least one of the oligonucleotides selected from the group consisting of:

an oligonucleotide comprising a base sequence of 5' atccagccgcaccttccgatac 3' (SEQ ID NO: 22); and an oligonucleotide comprising a base sequence of 5' atccagccgcaccttccggtac 3' (SEQ ID NO: 25).

\* \* \* \* \*

SEQUENCE LISTING

<160> NUMBER OF SEQ ID NOS: 68

<210> SEQ ID NO 1
<211> LENGTH: 23
<212> TYPE: DNA
<213> ORGANISM: Artificial Sequence
<220> FEATURE:
<223> OTHER INFORMATION: Primer

<400> SEQUENCE: 1
gcggcgtgcc taatacatgc aag                                    23

<210> SEQ ID NO 2
<211> LENGTH: 23
<212> TYPE: DNA
<213> ORGANISM: Artificial Sequence
<220> FEATURE:
<223> OTHER INFORMATION: Primer

<400> SEQUENCE: 2
gcggcaggcc taacacatgc aag                                    23

<210> SEQ ID NO 3
<211> LENGTH: 23
<212> TYPE: DNA
<213> ORGANISM: Artificial Sequence

```
<220> FEATURE:
<223> OTHER INFORMATION: Primer

<400> SEQUENCE: 3
gcggcaggct taacacatgc aag                                      23

<210> SEQ ID NO 4
<211> LENGTH: 23
<212> TYPE: DNA
<213> ORGANISM: Artificial Sequence
<220> FEATURE:
<223> OTHER INFORMATION: Primer

<400> SEQUENCE: 4
gcggtaggcc taacacatgc aag                                      23

<210> SEQ ID NO 5
<211> LENGTH: 23
<212> TYPE: DNA
<213> ORGANISM: Artificial Sequence
<220> FEATURE:
<223> OTHER INFORMATION: Primer

<400> SEQUENCE: 5
gcggcgtgct taacacatgc aag                                      23

<210> SEQ ID NO 6
<211> LENGTH: 23
<212> TYPE: DNA
<213> ORGANISM: Artificial Sequence
<220> FEATURE:
<223> OTHER INFORMATION: Primer

<400> SEQUENCE: 6
gcgggatgcc ttacacatgc aag                                      23

<210> SEQ ID NO 7
<211> LENGTH: 23
<212> TYPE: DNA
<213> ORGANISM: Artificial Sequence
<220> FEATURE:
<223> OTHER INFORMATION: Primer

<400> SEQUENCE: 7
gcggcatgcc ttacacatgc aag                                      23

<210> SEQ ID NO 8
<211> LENGTH: 23
<212> TYPE: DNA
<213> ORGANISM: Artificial Sequence
<220> FEATURE:
<223> OTHER INFORMATION: Primer

<400> SEQUENCE: 8
gcggcatgct taacacatgc aag                                      23

<210> SEQ ID NO 9
<211> LENGTH: 23
<212> TYPE: DNA
<213> ORGANISM: Artificial Sequence
<220> FEATURE:
<223> OTHER INFORMATION: Primer

<400> SEQUENCE: 9
gcggcgtgct taatacatgc aag                                      23
```

```
<210> SEQ ID NO 10
<211> LENGTH: 23
<212> TYPE: DNA
<213> ORGANISM: Artificial Sequence
<220> FEATURE:
<223> OTHER INFORMATION: Primer

<400> SEQUENCE: 10
gcggcaggcc taatacatgc aag                                              23

<210> SEQ ID NO 11
<211> LENGTH: 23
<212> TYPE: DNA
<213> ORGANISM: Artificial Sequence
<220> FEATURE:
<223> OTHER INFORMATION: Primer

<400> SEQUENCE: 11
gcgggatgct ttacacatgc aag                                              23

<210> SEQ ID NO 12
<211> LENGTH: 23
<212> TYPE: DNA
<213> ORGANISM: Artificial Sequence
<220> FEATURE:
<223> OTHER INFORMATION: Primer

<400> SEQUENCE: 12
gcggcgtgcc taacacatgc aag                                              23

<210> SEQ ID NO 13
<211> LENGTH: 23
<212> TYPE: DNA
<213> ORGANISM: Artificial Sequence
<220> FEATURE:
<223> OTHER INFORMATION: Primer

<400> SEQUENCE: 13
gcggcgtgca taacacatgc aag                                              23

<210> SEQ ID NO 14
<211> LENGTH: 23
<212> TYPE: DNA
<213> ORGANISM: Artificial Sequence
<220> FEATURE:
<223> OTHER INFORMATION: Primer

<400> SEQUENCE: 14
gcggcatgcc taacacatgc aag                                              23

<210> SEQ ID NO 15
<211> LENGTH: 23
<212> TYPE: DNA
<213> ORGANISM: Artificial Sequence
<220> FEATURE:
<223> OTHER INFORMATION: Primer

<400> SEQUENCE: 15
gcggcgcgcc taacacatgc aag                                              23

<210> SEQ ID NO 16
<211> LENGTH: 23
<212> TYPE: DNA
<213> ORGANISM: Artificial Sequence
<220> FEATURE:
<223> OTHER INFORMATION: Primer

<400> SEQUENCE: 16
```
gcggcgcgct taacacatgc aag                                           23

<210> SEQ ID NO 17
<211> LENGTH: 23
<212> TYPE: DNA
<213> ORGANISM: Artificial Sequence
<220> FEATURE:
<223> OTHER INFORMATION: Primer

<400> SEQUENCE: 17
gcgtcatgcc taacacatgc aag                                           23

<210> SEQ ID NO 18
<211> LENGTH: 23
<212> TYPE: DNA
<213> ORGANISM: Artificial Sequence
<220> FEATURE:
<223> OTHER INFORMATION: Primer

<400> SEQUENCE: 18
gcgataggct taacacatgc aag                                           23

<210> SEQ ID NO 19
<211> LENGTH: 23
<212> TYPE: DNA
<213> ORGANISM: Artificial Sequence
<220> FEATURE:
<223> OTHER INFORMATION: Primer

<400> SEQUENCE: 19
gcgacaggct taacacatgc aag                                           23

<210> SEQ ID NO 20
<211> LENGTH: 23
<212> TYPE: DNA
<213> ORGANISM: Artificial Sequence
<220> FEATURE:
<223> OTHER INFORMATION: Primer

<400> SEQUENCE: 20
gctacaggct taacacatgc aag                                           23

<210> SEQ ID NO 21
<211> LENGTH: 23
<212> TYPE: DNA
<213> ORGANISM: Artificial Sequence
<220> FEATURE:
<223> OTHER INFORMATION: Primer

<400> SEQUENCE: 21
acagaatgct taacacatgc aag                                           23

<210> SEQ ID NO 22
<211> LENGTH: 22
<212> TYPE: DNA
<213> ORGANISM: Artificial Sequence
<220> FEATURE:
<223> OTHER INFORMATION: Primer

<400> SEQUENCE: 22
atccagccgc accttccgat ac                                            22

<210> SEQ ID NO 23
<211> LENGTH: 22
<212> TYPE: DNA
<213> ORGANISM: Artificial Sequence

```
<220> FEATURE:
<223> OTHER INFORMATION: Primer

<400> SEQUENCE: 23
atccaaccgc aggttcccct ac                                              22

<210> SEQ ID NO 24
<211> LENGTH: 22
<212> TYPE: DNA
<213> ORGANISM: Artificial Sequence
<220> FEATURE:
<223> OTHER INFORMATION: Primer

<400> SEQUENCE: 24
atccagccgc aggttcccct ac                                              22

<210> SEQ ID NO 25
<211> LENGTH: 22
<212> TYPE: DNA
<213> ORGANISM: Artificial Sequence
<220> FEATURE:
<223> OTHER INFORMATION: Primer

<400> SEQUENCE: 25
atccagccgc accttccggt ac                                              22

<210> SEQ ID NO 26
<211> LENGTH: 22
<212> TYPE: DNA
<213> ORGANISM: Artificial Sequence
<220> FEATURE:
<223> OTHER INFORMATION: Primer

<400> SEQUENCE: 26
atccagcgcc aggttcccct ag                                              22

<210> SEQ ID NO 27
<211> LENGTH: 22
<212> TYPE: DNA
<213> ORGANISM: Artificial Sequence
<220> FEATURE:
<223> OTHER INFORMATION: Primer

<400> SEQUENCE: 27
atccagccgc aggttctcct ac                                              22

<210> SEQ ID NO 28
<211> LENGTH: 22
<212> TYPE: DNA
<213> ORGANISM: Artificial Sequence
<220> FEATURE:
<223> OTHER INFORMATION: Primer

<400> SEQUENCE: 28
atccagccgc acgttcccgt ac                                              22

<210> SEQ ID NO 29
<211> LENGTH: 23
<212> TYPE: DNA
<213> ORGANISM: Artificial Sequence
<220> FEATURE:
<223> OTHER INFORMATION: Primer

<400> SEQUENCE: 29
taccttgtta cgacttcacc cca                                             23
```

```
<210> SEQ ID NO 30
<211> LENGTH: 23
<212> TYPE: DNA
<213> ORGANISM: Artificial Sequence
<220> FEATURE:
<223> OTHER INFORMATION: Primer

<400> SEQUENCE: 30
taccttgtta cgacttcgtc cca                                             23

<210> SEQ ID NO 31
<211> LENGTH: 23
<212> TYPE: DNA
<213> ORGANISM: Artificial Sequence
<220> FEATURE:
<223> OTHER INFORMATION: Primer

<400> SEQUENCE: 31
taccttgtta cgacttagtc cca                                             23

<210> SEQ ID NO 32
<211> LENGTH: 23
<212> TYPE: DNA
<213> ORGANISM: Artificial Sequence
<220> FEATURE:
<223> OTHER INFORMATION: Primer

<400> SEQUENCE: 32
taccttgtta cgacttagcc cca                                             23

<210> SEQ ID NO 33
<211> LENGTH: 23
<212> TYPE: DNA
<213> ORGANISM: Artificial Sequence
<220> FEATURE:
<223> OTHER INFORMATION: Primer

<400> SEQUENCE: 33
taccttgtta cgacttagtc cta                                             23

<210> SEQ ID NO 34
<211> LENGTH: 23
<212> TYPE: DNA
<213> ORGANISM: Artificial Sequence
<220> FEATURE:
<223> OTHER INFORMATION: Primer

<400> SEQUENCE: 34
taccttgtta cgacttagcc cta                                             23

<210> SEQ ID NO 35
<211> LENGTH: 28
<212> TYPE: DNA
<213> ORGANISM: Artificial
<220> FEATURE:
<223> OTHER INFORMATION: probe

<400> SEQUENCE: 35
tcatcttgag gtatggaagg gaaagtgg                                        28

<210> SEQ ID NO 36
<211> LENGTH: 28
<212> TYPE: DNA
<213> ORGANISM: artificial
<220> FEATURE:
<223> OTHER INFORMATION: probe

<400> SEQUENCE: 36
```

-continued gtgttaggtg tctggaataa tctgggtg                    28

<210> SEQ ID NO 37
<211> LENGTH: 25
<212> TYPE: DNA
<213> ORGANISM: artificial
<220> FEATURE:
<223> OTHER INFORMATION: probe

<400> SEQUENCE: 37
accaagtctt gacatattac ggcgg                       25

<210> SEQ ID NO 38
<211> LENGTH: 26
<212> TYPE: DNA
<213> ORGANISM: artificial
<220> FEATURE:
<223> OTHER INFORMATION: probe

<400> SEQUENCE: 38
aaggattccg gtaaaggatg gggatg                      26

<210> SEQ ID NO 39
<211> LENGTH: 26
<212> TYPE: DNA
<213> ORGANISM: artificial
<220> FEATURE:
<223> OTHER INFORMATION: probe

<400> SEQUENCE: 39
tggaaacatg tcagtgagca atcacc                      26

<210> SEQ ID NO 40
<211> LENGTH: 27
<212> TYPE: DNA
<213> ORGANISM: artificial
<220> FEATURE:
<223> OTHER INFORMATION: probe

<400> SEQUENCE: 40
aagaatttcg gttatcgatg gggatgc                     27

<210> SEQ ID NO 41
<211> LENGTH: 29
<212> TYPE: DNA
<213> ORGANISM: artificial
<220> FEATURE:
<223> OTHER INFORMATION: probe

<400> SEQUENCE: 41
aagttttcca cgtgtggaat tttgtatgt                   29

<210> SEQ ID NO 42
<211> LENGTH: 24
<212> TYPE: DNA
<213> ORGANISM: artificial
<220> FEATURE:
<223> OTHER INFORMATION: probe

<400> SEQUENCE: 42
aaggcagcta cctggtgaca ggat                        24

<210> SEQ ID NO 43
<211> LENGTH: 30
<212> TYPE: DNA
<213> ORGANISM: artificial

```
<220> FEATURE:
<223> OTHER INFORMATION: probe

<400> SEQUENCE: 43
aatatcaaag gtgagccagt acaggatgga                                    30

<210> SEQ ID NO 44
<211> LENGTH: 28
<212> TYPE: DNA
<213> ORGANISM: artificial
<220> FEATURE:
<223> OTHER INFORMATION: probe

<400> SEQUENCE: 44
ccgtagtaag ctcttgaaac tgggagac                                      28

<210> SEQ ID NO 45
<211> LENGTH: 28
<212> TYPE: DNA
<213> ORGANISM: artificial
<220> FEATURE:
<223> OTHER INFORMATION: probe

<400> SEQUENCE: 45
tcccaatgac atctccttaa tcggagag                                      28

<210> SEQ ID NO 46
<211> LENGTH: 27
<212> TYPE: DNA
<213> ORGANISM: artificial
<220> FEATURE:
<223> OTHER INFORMATION: probe

<400> SEQUENCE: 46
aaccaaagga gcaatccgct atgagat                                       27

<210> SEQ ID NO 47
<211> LENGTH: 25
<212> TYPE: DNA
<213> ORGANISM: artificial
<220> FEATURE:
<223> OTHER INFORMATION: probe

<400> SEQUENCE: 47
gagcgtaggc ggatgattaa gtggg                                         25

<210> SEQ ID NO 48
<211> LENGTH: 29
<212> TYPE: DNA
<213> ORGANISM: artificial
<220> FEATURE:
<223> OTHER INFORMATION: probe

<400> SEQUENCE: 48
cccttgcatt actcttaatc gaggaaatc                                     29

<210> SEQ ID NO 49
<211> LENGTH: 22
<212> TYPE: DNA
<213> ORGANISM: artificial
<220> FEATURE:
<223> OTHER INFORMATION: probe

<400> SEQUENCE: 49
ggaaagccca gacggcaagg ga                                            22
```

-continued

```
<210> SEQ ID NO 50
<211> LENGTH: 26
<212> TYPE: DNA
<213> ORGANISM: artificial
<220> FEATURE:
<223> OTHER INFORMATION: probe

<400> SEQUENCE: 50
cctctcaagc gggatctcta atccga                                          26

<210> SEQ ID NO 51
<211> LENGTH: 23
<212> TYPE: DNA
<213> ORGANISM: artificial
<220> FEATURE:
<223> OTHER INFORMATION: probe

<400> SEQUENCE: 51
tgccccatgt tgccagcatt agg                                             23

<210> SEQ ID NO 52
<211> LENGTH: 28
<212> TYPE: DNA
<213> ORGANISM: artificial
<220> FEATURE:
<223> OTHER INFORMATION: probe

<400> SEQUENCE: 52
ttttcgcatg gaggaatcat gaaagcta                                        28

<210> SEQ ID NO 53
<211> LENGTH: 21
<212> TYPE: DNA
<213> ORGANISM: artificial
<220> FEATURE:
<223> OTHER INFORMATION: probe

<400> SEQUENCE: 53
agatgcgccg gtgcccttc g                                                21

<210> SEQ ID NO 54
<211> LENGTH: 26
<212> TYPE: DNA
<213> ORGANISM: artificial
<220> FEATURE:
<223> OTHER INFORMATION: probe

<400> SEQUENCE: 54
agtcgggaag aagtcagtga cggtac                                          26

<210> SEQ ID NO 55
<211> LENGTH: 24
<212> TYPE: DNA
<213> ORGANISM: artificial
<220> FEATURE:
<223> OTHER INFORMATION: probe

<400> SEQUENCE: 55
gagtacgtgc gcaagcatga aact                                            24

<210> SEQ ID NO 56
<211> LENGTH: 24
<212> TYPE: DNA
<213> ORGANISM: artificial
<220> FEATURE:
<223> OTHER INFORMATION: probe

<400> SEQUENCE: 56
```
gaagactgcc cgcaagggtt gtaa                                          24

<210> SEQ ID NO 57
<211> LENGTH: 25
<212> TYPE: DNA
<213> ORGANISM: artificial
<220> FEATURE:
<223> OTHER INFORMATION: probe

<400> SEQUENCE: 57
gtgtactgga ggtacgtgga acgtg                                         25

<210> SEQ ID NO 58
<211> LENGTH: 24
<212> TYPE: DNA
<213> ORGANISM: artificial
<220> FEATURE:
<223> OTHER INFORMATION: probe

<400> SEQUENCE: 58
gcatgaggct gagaggtctc ttcc                                          24

<210> SEQ ID NO 59
<211> LENGTH: 28
<212> TYPE: DNA
<213> ORGANISM: artificial
<220> FEATURE:
<223> OTHER INFORMATION: probe

<400> SEQUENCE: 59
ttatagctgt aagataggca tgcgtccc                                      28

<210> SEQ ID NO 60
<211> LENGTH: 26
<212> TYPE: DNA
<213> ORGANISM: artificial
<220> FEATURE:
<223> OTHER INFORMATION: probe

<400> SEQUENCE: 60
aacgggcgat acgagtattg cattga                                        26

<210> SEQ ID NO 61
<211> LENGTH: 25
<212> TYPE: DNA
<213> ORGANISM: artificial
<220> FEATURE:
<223> OTHER INFORMATION: probe

<400> SEQUENCE: 61
atataccgtc aagcttccac agcga                                         25

<210> SEQ ID NO 62
<211> LENGTH: 25
<212> TYPE: DNA
<213> ORGANISM: artificial
<220> FEATURE:
<223> OTHER INFORMATION: probe

<400> SEQUENCE: 62
tttgaaaggc gcttttgcgt cactg                                         25

<210> SEQ ID NO 63
<211> LENGTH: 30
<212> TYPE: DNA
<213> ORGANISM: artificial

```
<220> FEATURE:
<223> OTHER INFORMATION: probe

<400> SEQUENCE: 63
caaggatgag agtagaacgt tcatcccttg                                        30

<210> SEQ ID NO 64
<211> LENGTH: 30
<212> TYPE: DNA
<213> ORGANISM: artificial
<220> FEATURE:
<223> OTHER INFORMATION: probe

<400> SEQUENCE: 64
caaggatgag agtagaatgt tcatcccttg                                        30

<210> SEQ ID NO 65
<211> LENGTH: 27
<212> TYPE: DNA
<213> ORGANISM: artificial
<220> FEATURE:
<223> OTHER INFORMATION: probe

<400> SEQUENCE: 65
cctgggaatg gcatctaaga ctggtca                                           27

<210> SEQ ID NO 66
<211> LENGTH: 28
<212> TYPE: DNA
<213> ORGANISM: artificial
<220> FEATURE:
<223> OTHER INFORMATION: probe

<400> SEQUENCE: 66
gaggaaggcg ttgatgctaa tatcatca                                          28

<210> SEQ ID NO 67
<211> LENGTH: 24
<212> TYPE: DNA
<213> ORGANISM: artificial
<220> FEATURE:
<223> OTHER INFORMATION: probe

<400> SEQUENCE: 67
gagcaaagca ggggaacttc ggtc                                              24

<210> SEQ ID NO 68
<211> LENGTH: 1486
<212> TYPE: DNA
<213> ORGANISM: Peptoniphilus asaccharolyticus

<400> SEQUENCE: 68
ctcaggacga acgctggcgg cgcgcttaac acatgcaagt cgagcgatga agctttaaca      60
gattccttcg ggatgaagat aaagyggatt agcggcggac gggtgagtaa cacgtgagta     120
acctgccttt gacatcggga tagcctcggg aaaccgggat taataccgaa taaaatccta     180
catacacatg tacataggat caaaactacg gtggtcttag atggactcgc gtcccattag     240
ctagttggtg gagtaaaagc ctaccaaggc gacgatgggt agccggcctg agagggtgat     300
cggccacatt ggaactgaga acggtccaa actcctacgg gaggcagcag tggggaatat     360
tgcacaatgg aggaaactct gatgcagcga cgccgcgtga atgaagaatg ccttagggca     420
gtaaagttct tttatatggg aagataatga cggtaccata agaaaagcc ccggctaact     480
acgtgccagc agccgcggta atacgtaggg ggctagcgtt gtccggaatc actgggcgta     540
```

```
aagggttcgc aggcggaaat gcaagtcaga tgtaaaaggc agtagcttaa ctactgtaag     600
catttgaaac tgtatatctt gagaagtgta gaggtaagtg gaatttttag tgtagcggtg     660
aaatgcgtag atattaaaaa gaataccggt ggcgaaggcg acttactggg cacattctga     720
cgctgaggaa cgaaagcgtg ggtagcaaac aggattagat accctggtag tccacgctgt     780
aaacgatgag tgctaggtgt cggcaaaagt cggtgccgca gttaacacat taagcactcc     840
gcctggggag tacgtgcgca agcatgaaac tcaaaggaat tgacggggac ccgcacaagc     900
agcggagcat gtggtttaat tcgaagcaac gcgaagaacc ttaccagggc ttgacatata     960
gaggacatat ttagagataa ataatcttct tcggaagcct ctatacaggt ggtgcatggt    1020
tgtcgtcagc tcgtgtcgtg agatgttggg ttaagtcccg caacgagcgc aacccttata    1080
tctagttgcc agcatttcgg atgggaactc tagatagact gccgatgaca aatcggagga    1140
aggtggggat gacgtcaaat catcatgccc tatatgccct gggcaacaca cgtgctacaa    1200
tggaaggtac aaagggaagc caaatcgcga ggtggagcaa acctcaaaaa gcctttccca    1260
gttcggattg ttctctgcaa ctcgagaaca tgaagctgga gttgctagta atcgcagatc    1320
agaatgctgc ggtgaatgcg ttcccgggtc ttgtacacac cgcccgtcac accatgggag    1380
cttgtaatac ccgaagcctg tgagctaacc gcaaggtgca gcagtcgaag gtaggatgag    1440
tgactggggt gaagtcgtaa caaggtagcc gtatcggaag gtgcgg                   1486
```